Figure 1:
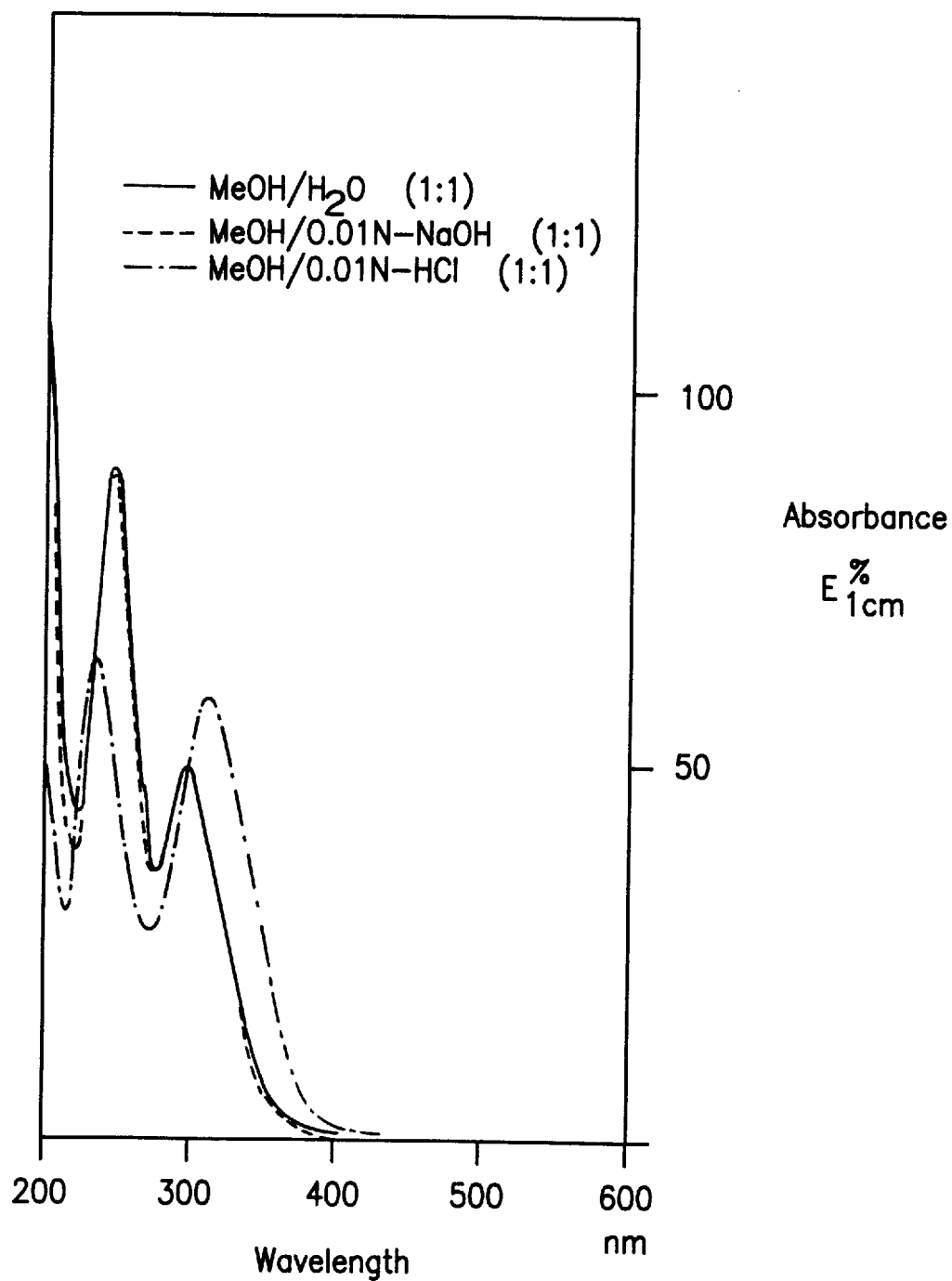
Figure 2:
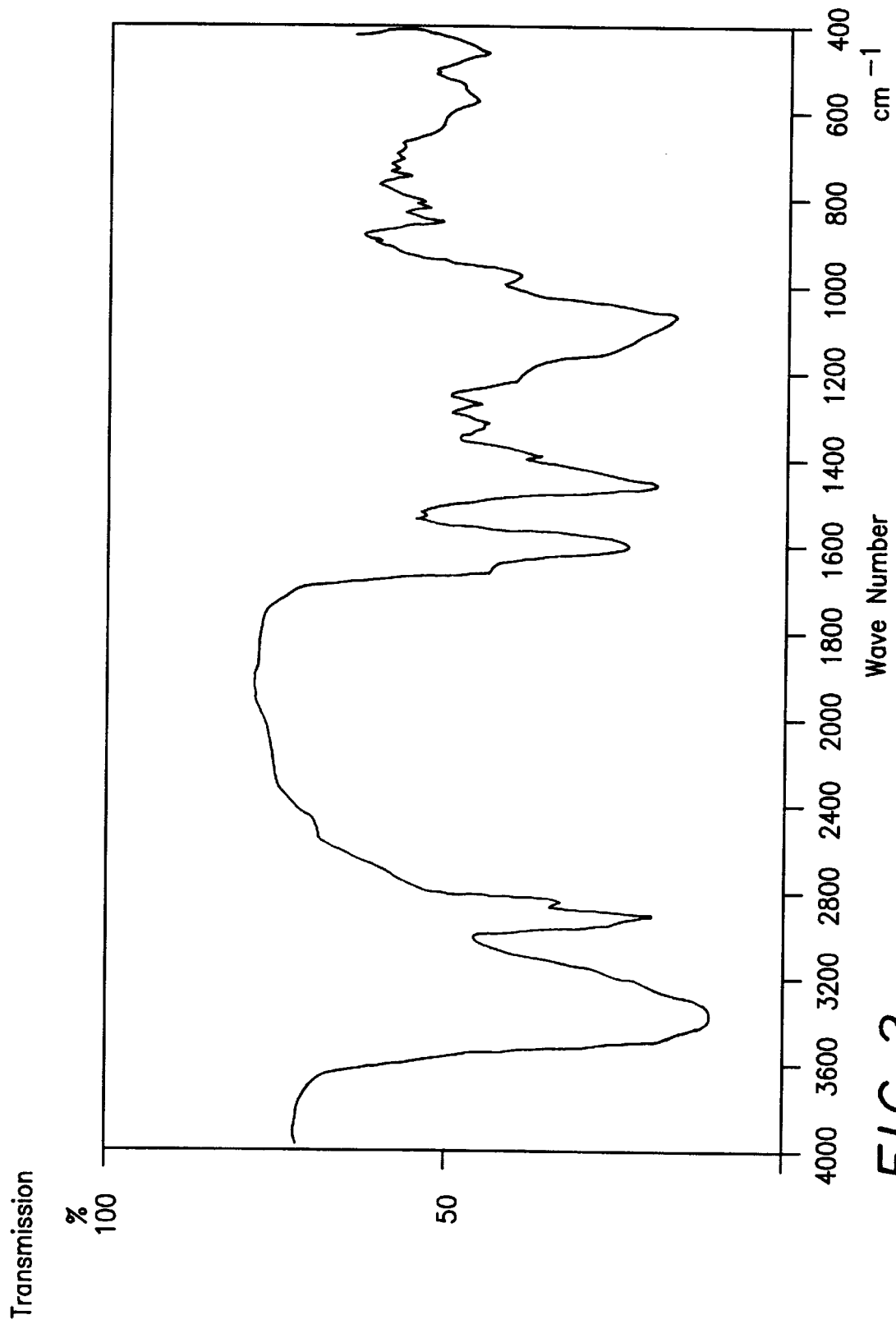
Figure 3:
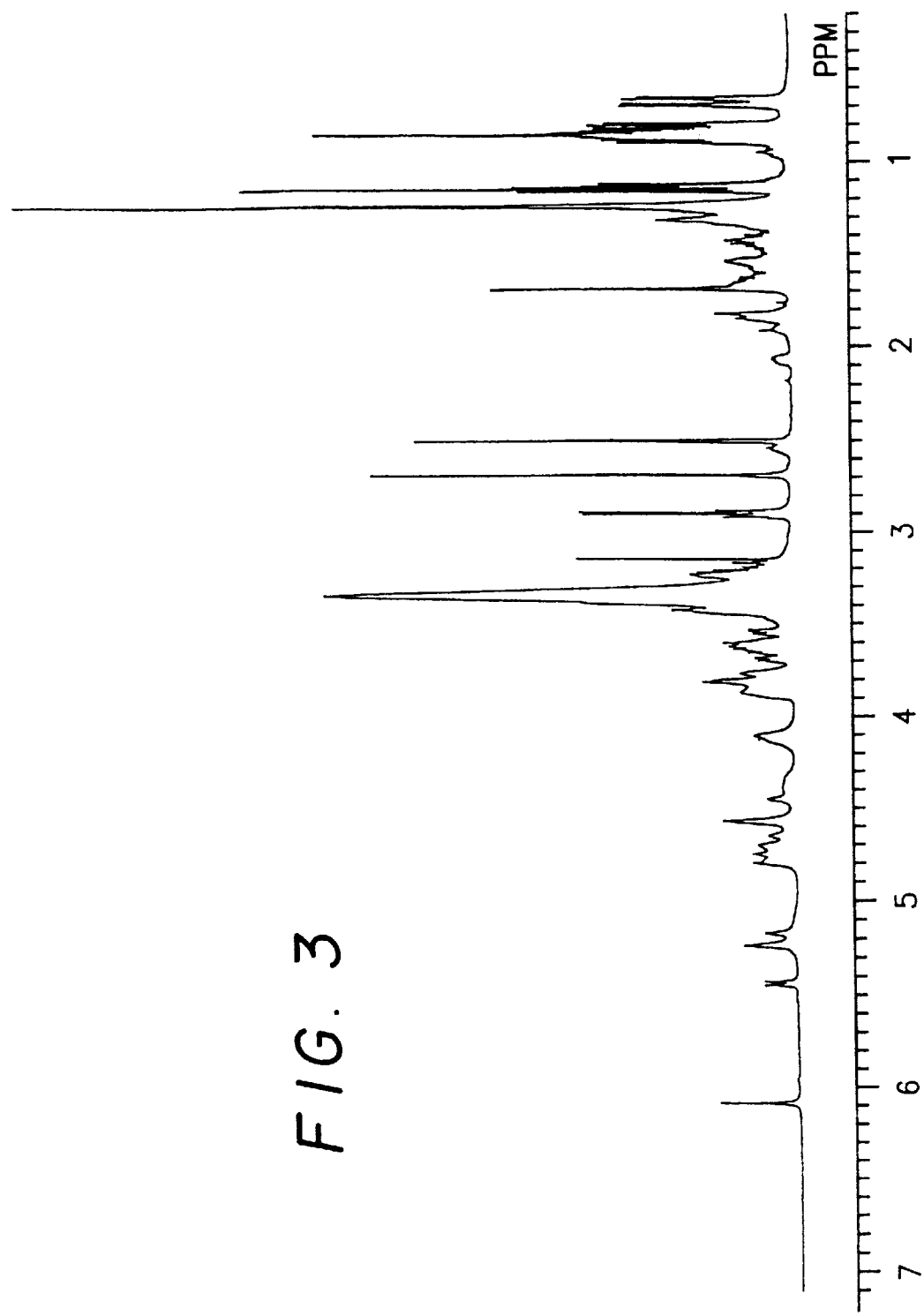
Figure 4:
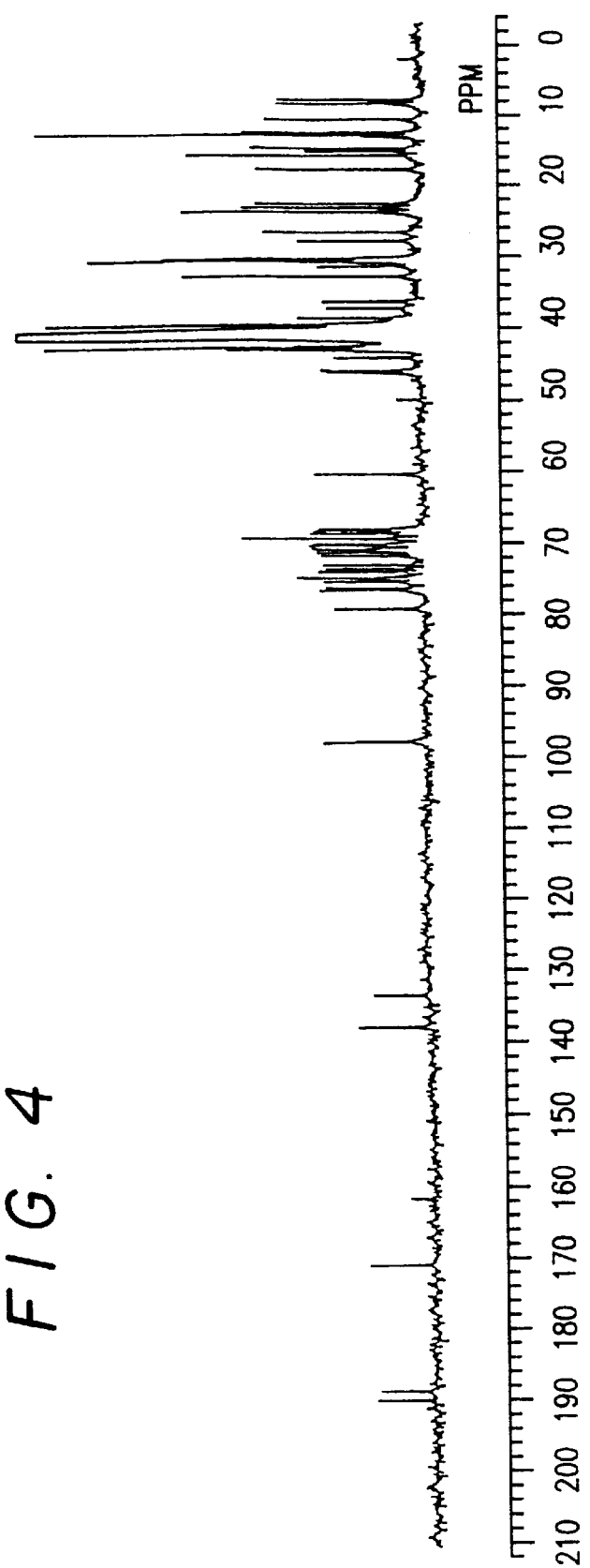

United States Patent [19]

Ono et al.

[11] Patent Number: 5,773,263

[45] Date of Patent: Jun. 30, 1998

[54] PRODUCTION AFLASTATIN A FROM STREPTOMYCES SP., A PHARMACEUTICAL COMPOSITION AND METHODS OF USE

[75] Inventors: Makoto Ono, Kawasaki; Akinori Suzuki, Chigasaki; Akira Isogai; Shouhei Sakuda, both of Chiba, all of Japan

[73] Assignee: Morinaga & Co., Ltd., Tokyo, Japan

[21] Appl. No.: 810,368

[22] Filed: Mar. 3, 1997

[30] Foreign Application Priority Data

Mar. 4, 1996 [JP] Japan .................................. 8-073258

[51] Int. Cl.[6] .............................. C12P 17/16; C12N 1/20; A01N 43/36; C07D 205/00

[52] U.S. Cl. ........................ 435/118; 435/253.5; 514/423; 548/953

[58] Field of Search ............................ 548/953; 514/423; 435/118, 253.5

Primary Examiner—Jon P. Weber
Assistant Examiner—Susan Hanley
Attorney, Agent, or Firm—Beveridge, DeGrandi, Weilacher & Young, LLP

[57] ABSTRACT

The antibiotic aflastatin A or its salt and its production by Streptomyces sp. MRI 142, FERM BP-5841 is presented. Aflastatin A is incorporated into a pharmaceutical composition and is employed as an aflatoxin contamination inhibitor, antimicrobial agent, antifungal agent and antitumor agent.

13 Claims, 4 Drawing Sheets

PRODUCTION AFLASTATIN A FROM STREPTOMYCES SP., A PHARMACEUTICAL COMPOSITION AND METHODS OF USE

BACKGROUND OF THE INVENTION

(1) Field of the Invention

The present invention relates to an antibiotic aflastatin A or its salt; an aflatoxin contamination inhibitor, an antimicrobial agent, an antifungus agent and an antitumor agent containing it; aflatoxin contamination inhibiting method and tumor-inhibiting method employing it; and a process for preparing it.

(2) Background Information

Aflatoxin produced from some mildew belonging to Aspergillus sp. has been known to have a potent carcinogenicity. Further, such aflatoxin producing-mildew have been known to infect agricultural commodities such as corn or peanuts and produce the aflatoxin, resulting in contamination of these agricultural commodities.

As pharmaceuticals intended to prevent the aflatoxin contamination, dichlorovos and antibiotic Iturin A have heretofore been known. However, these pharmaceuticals have not been practiced until now.

Conventional pharmaceuticals such as antibiotic Iturin A are the ones inhibiting the aflatoxin contamination by controlling the propagation of aflatoxigenic fungi. Accordingly, once drug-resistant strains or the like emerge, such pharmaceuticals are no longer capable of inhibiting the pervasion thereof.

SUMMARY OF THE INVENTION

In order to prevent the aflatoxin contamination, the present inventors have conducted screening search for antibiotics which inhibit biosynthesis of such compounds by, particularly, the aflatoxigenic fungi. The purpose is to minimize the possibility of emergence and pervasion of drug-resistant strains from the aflatoxigenic fungi, by inhibiting only the biosynthesis of aflatoxin and not by inhibiting the growth of the aflatoxigenic fungi. Namely, such a purpose is based on the following speculation. The production of aflatoxin by the aflatoxigenic fungi, is not indispensable biochemical demand for the growth of said strains. Accordingly, it is expected that, by the use of pharmaceuticals which inhibit only biosynthesis of aflatoxin, selection of the resistant strains by the pharmaceuticals themselves are not made, and the pervasion of the resistant strains can be inhibited.

As a result of the above search, the present inventors have succeeded to isolate a novel antibiotic having an activity of inhibiting the production of aflatoxin, from the culture medium of some strains which belong to Streptomyces sp. collected from a soil sample in Zushi-shi, Kanagawa prefecture, Japan. They named this antibiotic, aflastatin A. Further, they have found also that this aflastatin A is also effective as an antimicrobial agent, an antifungus agent and an antitumor agent, and accomplished the present invention based on such discoveries. As a result of identification, it was found that the antibiotic aflastatin A is different from other antibiotics known in the prior art.

Namely, the present invention is to provide an antibiotic aflastatin A of the following chemical formula (1) or its salt.

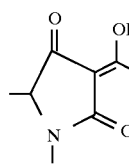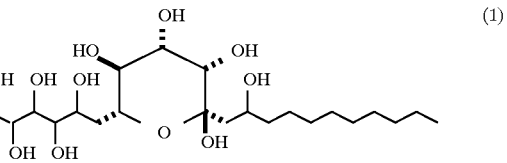 (1)

The present invention also provides an aflatoxin contamination inhibitor comprising the above antibiotic aflastatin A or its salt and at least one of a solid carrier, a liquid carrier and an emulsion dispersant.

The present invention further provides an antimicrobial agent comprising the above antibiotic aflastatin A or its salt and at least one of a carrier, an excipient and a diluent.

The present invention further provides an antifungus agent comprising the above antibiotic aflastatin A or its salt and at least one of a carrier, an excipient and a diluent.

The present invention further provides an antitumor agent comprising the above antibiotic aflastatin A or its salt and at least one of a carrier, an excipient and a diluent.

The present invention further provides an aflatoxin contamination inhibiting method, which comprises spraying a chemical containing from 10 to 5,000 ppm of the above antibiotic aflastatin A or its salt on plants.

The present invention further provides a tumor-inhibiting method, which comprises administering an effective amount of the above antibiotic aflastatin A or its salt.

The present invention further provides a process for preparing the antibiotic aflastatin A or its salt, which comprising culturing the producing strains of antibiotic aflastatin A which belong to Streptomyces sp., and isolating the antibiotic aflastatin A or its salt from a culture medium.

In a preferred et of the present invention, as the aflastatin A producing strains which belong to Streptomyces sp., Streptomyces sp. MRI 142, FERM BP-5841 is used.

The antibiotic aflastatin A or its salt of the present invention, intensely inhibit the production of the aflatoxin by the aflatoxigenic fungi such as *Aspergillus parasiticus* and exhibit excellent effects for the inhibition of the aflatoxin contamination by the aflatoxigenic fungi, as indicated in the examples shown below.

Further, as indicated in the antimicrobial spectrum indicated below, the aflastatin A or its salt of the present invention shows excellent antimicrobial activity against fungi such as *Candida albicans* and *Trichophyton mentagropytes* and bacteria such as *Staphylococcus aureus*. Accordingly, the aflastatin A or its salt of the present invention is expected to exhibit excellent effects as a therapeutic medicine for infectious disease of humans and animals. Further, it shows excellent antimicrobial effect against

*Pyricularia oryzae* as the pathogen of rice blast disease, and thus can be used as a preventive pesticide for rice blast disease.

Further, as indicated in the examples mentioned below, from the animal tests employing mice, the aflastatin A or its salt was confirmed to remarkably inhibit the propagation of mouse adenocarcinoma 755 subcutaneously transplanted. Accordingly, the aflastatin A or its salt of the present invention is expected to exhibit excellent effects as an antitumor agent.

BRIEF DESCRIPTION OF THE DRAWINGS

FIG. 1 is a graph showing an ultraviolet absorption spectrum of a diethylamine salt of the antibiotic aflastatin A of the present invention.

FIG. 2 is a graph showing an infrared absorption spectrum of a diethylamine salt of the antibiotic aflastatin A.

FIG. 3 is a graph showing $^1$H-NMR spectrum of the antibiotic aflastatin A.

FIG. 4 is a graph showing $^{13}$C-NMR spectrum of the antibiotic aflastatin A.

DESCRIPTION OF THE PREFERRED EMBODIMENTS

Physico-chemical properties and biological properties of the novel antibiotic aflastatin A of the present invention are as follows:

a) Appearance: white powder b) Molecular formula and elemental analysis value: $C_{62}H_{115}O_{24}N$ Found value: C: 53.96%, H: 8.95%, O: 35.77%, N: 1.08% Calculated value (calculated as $C_{62}H_{115}O_{34}N.7H_2O$): C: 53.78%, R: 9.39%, O: 35.82%, N: 1.04% c) $[\alpha]^{19}_D$=−2.60° (C=0.545, DMSO)

d) Molecular weight: 1257 FAB-MASS m/z 1280 $(M+Na)^+$ FAB-MASS m/z 1256 $(M-H)^-$ e) Major UV spectrometry UV spectra of aflastatin A in the form of a diethylamine salt are shown in FIG. 1.

λmax ($MeOH/H_2O$, 1:1) m($E^{1\%}_{1\ cm}$); 299(49), 247(89) (MeOH/0.01N-NaOH, 1:1) nm($E^{1\%}_{1\ cm}$); 299(49), 247 (88) (MeOH/0.01N-HCl, 1:1) nm($E^{1\%}_{1\ cm}$); 314(58), 237(63)

f) Major IR spectrometry

IR spectra of aflastatin A in the form of a diethylamine salt on a potassium bromide wafer are shown in FIG. 2.

νmax (KBr wafer); 3380, 2930, 2850, 1600, 1450, 1380, 1310, 1275, 1060, 960, 845, 800, 740 $cm^{-1}$ g) NMR spectra $^1$H-NMR spectrum of the aflastatin A in the form of a diethylamine salt in DMSO-$d_6$ at 500 MHz are shown in FIG. 3.

$^{13}$C-NMR spectrum of the aflastatin A in the form of a diethylamine salt in DMSO-$d_6$ at 125 MHz are shown in FIG. 4.

h) Solubility

Soluble in dimethyl sulfoxide; slightly soluble in methanol, aqueous ethanol, aqueous butanol and glycerol; practically insoluble in water and other organic solvents i) Color reaction Positive to ferric chloride reaction Negative to ninhydrin reaction j) Antimicrobial spectra Conditions for the measurements of the antimicrobial sepctra are as follows:

80 mg of aflastatin A was dissolved in 4 ml of dimethyl sulfoxide (DMSO). This solution was diluted with DMSO to prepare a dilution series by two times as test solutions. The test solutions were filtrated with a filter and sterilized. 50 μl of each of them was added to 10 ml of a sterilized agar medium at 60° C. to prepare a dilution series of agar media. To each of the agar media, test strains were inoculated for antimicrobial activity. Minimum inhibitory concentrations (MICs) in this teat are shown in Table 1. Media used for the tests are as follows:

A: Nutrient agar (manufactured by Nihon Suisan K.K.)

B: Potato dextrose agar (manufactured by Nihon Suisan K.K.)

C: Sabouraud agar (manufactured by Nihon Suisan K.K.)

TABLE 1

| Organisms | Medium | Temp. (°C.) | Period (hrs) | MIC (g/ml) |
|---|---|---|---|---|
| *Bacillus subtilis* IAM 1145 | A | 37 | 24 | 0.39 |
| *Staphylococcus aureus* IFO 13276 | A | 37 | 24 | 0.78 |
| *Escherichia coli* IFO 14249 | A | 37 | 24 | >100 |
| *Psuedomonas aeruginosa* IAM 1514 | A | 37 | 24 | >100 |
| *Saccharomyces cerevisiae* IFO 0250 | C | 30 | 48 | <0.19 |
| *Candida albicans* IFO 1594 | C | 30 | 48 | 0.39 |
| *Trichophyton mentagrophytes* IFO 5809 | C | 30 | 48 | 0.39 |
| *Fusarium graminearum* ATCC 34909 | B | 27 | 48 | >100 |
| *Aspergillus parasiticus* NRRL 2999 | B | 27 | 48 | >100 |
| *Pyricularia oryzae* IFO 30732 | B | 27 | 48 | >0.19 | k) Toxicity

Aflastatin A was suspended in a 0.25% carboxymethylcellulose solution and the suspension was administered to ddy series male mice. The $LD_{50}$ value was 6.17 mg/kg by single intraperitoneal administration. By single oral administration, no mice died in an administered amount of 1,000 mg/kg or less.

The antibiotic aflastatin A is prepared by culturing aflastatin A producing fungi which belong to Streptomyces sp., and isolating aflastatin A from the cultured medium.

As the aflastatin A producing fungi, any microorganisms can be used without limitation so long as they belong to the Streptomyces sp. and are capable of producing aflastatin A. For example, Streptomyces Sp. MRI 142 strain which was collected from a soil sample in the compound of Jinmu-ji, Zushi-shi, Kanagawa prefecture, Japan, and deposited as FERM BP-5841 to National Institute of Bioscience and Human-Technology of Agency of Industrial Science and Technology on Dec. 26, 1995, and its natural and artificial variants, may preferably be employed.

Since the above Streptomyces sp. MRI 142 strain has fungological characteristics as indicated below, it apparently belongs to Streptomyces sp. According to the characteristics, strain MRI 142 is judged to be most similar to *Streptomyces griseochromogenes* among the species described in "BERGEY'S Manual of Determinative Bacteriolog" 8th Ed (1975).

Fungological characteristics of Streptomyces sp. MRI 142 strain are indicated below. Here, the media used in the following items c) to e) were prepared in accordance with the methods described on pages 48 to 55 of "Experimental methods for identification of Antinomycetes" (compiled by Nihon Antinomycetes Society, published in 1988).

a) Morphological observation

The above strain was cultured at 27° C. for 9 days on inorganic salts-starch agar "ISP-4 medium" (manufactured by Difco Co.). Under electronic microscope observation, aerial hypha is mainly in the form of spiral, and thus classified into spiralis type. The spores were cylindrical or oval, and the spore surfaces were spiny.

b) Cell wall

The above strain was cultured on an liquid medium of tryptone-yeast broth "ISP-1 medium" (manufactured by Difco Co.), and this strain was hydrolyzed in 6N hydrochloric acid at 105° C. for 18 hours. By cellulose thin layer chromatography, LL-diaminopymeric acid was detected and no meso-diaminopymeric acid was detected.

e) Growth on various media

Growth conditions after cultivation of the strain at 27° C. for two weeks, are shown below. The color names are based on Hyoujyun Shikihyou (Nihon Kikaku Kyoukai).

1) Yeast-malt extract agar "ISP-2 medium" (manufactured by Difco Co.)
Growth: good
Aerial hypha: thin, powdery
Color name: white
Reverse side of colony: 5Y7/8 (dull yellow)
Soluble pigment: none 2) Oatmeal agar (in accordance with "ISP-3 medium")
Growth: good
Aerial hypha: good, powdery
Color name: 2.5Y4/2 (grayish yellow-brown)
Reverse side of colony: none
Soluble pigment: none 3) Inorganic salts-starch agar "ISP-4 medium" (manufactured by Difco Co.)
Growth: good
Aerial hypha: thin, powdery
Color name: 10Y5/2 (olive gray)
Reverse side of colony: 10Y6/6 (dull yellow)
Soluble pigment: none 4) Glycerol-asparagine agar (in accordance with "ISP-5 medium")
Growth: good
Aerial hypha: thin, powdery
Color name: 5Y9/2 (yellowish white)
Reverse side of colony: 7.5Y9/2 (yellowish white)
Soluble pigment: none 5) Tyrosine agar (in accordance with "ISP-7 medium")
Growth: good
Aerial hypha: thin, powdery
Color name: white
Reverse side of colony: 7.5Y6/6 (olive gray)
Soluble pigment: 5Y5/6 (light olive), upon dropwise addition of 0.05N-NaOH, 2.5Y6/8 (pearl yellow brown)

6) Sucrose-nitrate agar
Growth: poor
Aerial hypha: thin, powdery
Color name: 5Y7/2 (light olive gray)
Reverse side of colony: none
Soluble pigment: none 7) Czapek-Dox agar medium
Growth: poor
Aerial hypha: thin, powdery
Color name: 7.5Y4/2 (olive)
Reverse side of colony: none
Soluble pigment: none 8) Glucose-asparagine agar
Growth: good
Aerial hypha: scant, powdery
Color name: white
Reverse side of colony: 10Y9/1 (white)
Soluble pigment: none 9) Nutrient agar
Growth: good
Aerial hypha: none
Color name: none
Reverse side of colony: 7.5Y8/6 (pearl olive)
Soluble pigment: none 10) Peptone-yeast-iron agar (in accordance with "ISP-6 medium")
Growth: moderate
Aerial hypha: none
Color name: none
Reverse side of colony: 5Y7/3 (light olive gray)
Soluble pigment: 2.5YR4/2 (brown)
Upon dropwise addition of 0.05N-HCl, 7.5Y8/6 (pearl olive)
Upon dropwise addition of 0.05N-NaOH, 2.5YR6/10 (yellowish yellow red)

11) Triptone-yeast extra agar (in accordance with "ISP-1 medium")
Growth: moderate
Aerial hypha: scant, powdery
Color name: white
Reverse side of colony: 7.5Y9/2 (yellowish white)
Soluble pigment: none d) Utilization of carbon sourse For the above strain, the utilization of carbon sourse on Pridham and Gottlieb agar medium, is as follows:

| | |
|---|---|
| D-Glucose | utilization |
| L-Arabinose | utilization |
| D-Xylose | utilization |
| D-Fructose | utilization |
| Sucrose | no utilization |
| L-Rhamnose | no utilization |
| Raffinose | utilization |
| Inositol | utilization |
| D-Mannitol | utilization |
| Galactose | utilization |
| Salicin | utilization | e) Physiological properties

The growth temperature range of the above strain is from 20° to 37° C., and optimum growth temperature range is from 27° to 37° C. Physiological properties when cultured at 20° to 37° C. are indicated in Table 2.

TABLE 2

| Physiological properties | Medium | Conditions | Reaction |
|---|---|---|---|
| Starch hydrolysis | Inorganic salts-starch agar (ISP-4 medium) | 27° C., 7 days | Reaction |
| Milk liquefaction | Skim milk (Difco Co.) | 27° C. and 37° C., up to 10 days | Reaction |
| Milk coagulation | Skim milk (Difco Co.) | 27° C. and 37° C., up to 10 days | No Reaction |

TABLE 2-continued

| Physiological properties | Medium | Conditions | Reaction |
| --- | --- | --- | --- |
| Gelatin liquefaction | Gelatin peptone glucose | 20° C. and 27° C., by 21st day | No Reaction |
| Cellulose hydrolysis | Filter paper | 27° C., by 14th day | No Reaction |
| Formation of nitrous acid | 0.1% potassium nitride-containing broth (in accordance with ISP-8 medium | 27° C., by 21st day | Doubtful |
| Melanin production | ISP-1, ISP-6 and ISP-7 media | 27° C., by 14th day | Reaction |
| NaCl tolerance | 4–13% NaCl-containing ISP-2 media | 27° C., by 14th day | 7% or less |

The antibiotic aflastatin A is produced by propagating aflastatin A producing strains in a nutrient medium containing anabolic carbon sources and nitrogen sources under aerobic condition by, for example, shake culture or liquid culture.

Preferred carbon sources for the nutrient medium are glucose, starch, fructose and glycerol. Further, preferred nitrogen sources are yeast extract, peptone, gluten powder, cotton seed powder, soy bean powder, corn steep liquor, dried yeast and wheat malt; ammonium salts such as ammonium nitrate, ammonium sulfate and ammonium phosphate; and inorganic and organic nitrogen compounds such as urea and amino acid. It is preferred to use the carbon sources and nitrogen sources in combination. However, there is no necessity to use the ones of high purity, and the ones of low purity may be used so long as they contain small amount of growth factors and a substantial amount of inorganic nutrients.

Further, as the case requires, an inorganic salt such as sodium carbonate, calcium carbonate, sodium phosphate, potassium phosphate, sodium chloride, potassium chloride, sodium iodide, potassium iodide, magnesium salts, copper salts, cobalt salts, zinc salts or iron salts, may be added to the medium.

Further, particularly when the medium remarkably foam, an antifoaming agent such as liquid paraffin, fatty oil, vegetable oil, mineral oil or silicone, may be added.

When the aflastatin A is produced in a large scale, it is preferred to use a submerged culture. Further, when produced in a small scale, it is preferred to conduct shake culture in a flask, a bottle or the like, or surface culture.

Further, when the culture is carried out in a large size tank, it is preferred to use a propagation type aflastatin A producing strains for the inoculation to the production tank. Accordingly, it is preferred to inoculate spores or mycelia of aflastatin A to a medium of a relatively small amount, and culture the inoculated medium, thereby producing a seed culture of the aflastatin A producing strains, and then transfer the seed culture to a large size tank. The medium used for the production of the propagation type inoculation material, may be substantially the same as or different from the medium used for the production of the aflastatin A.

As the stirring and aeration of a culture mixture, various methods may be employed. For example, a method wherein a propeller or a similar mechanical stirring device is used, a method wherein a fermentation tank is rotated or shaken, or a method wherein a sterile air is brown to the medium, may preferably used.

Fermentation is preferably carried out at a temperature of from 20° to 37° C., more preferably from 25° to 37° C., for from 50 to 200 hours. It is preferred to determine the temperature and period of time from these ranges depending upon the various conditions and size for the fermentation.

After completion of the fermentation, aflastatin A is recovered from the culture medium, and, as the case requires, purify it. However, its method is not particularly limited. For example, a method wherein solvent extraction is carried out by using one or more solvents, and the extract is relatively concentrated by evaporation, distillation or the like, then the concentrate is purified by precipitation, recrystallization, chromatography or the like, may be employed. When the solvent extraction is carried out, for example, an organic solvent such as methanol, dimethylsulfoxide, butanol, ethyl acetate or acetone, may preferably be used.

In the production method of the present invention, particularly, when calcium carbonate is added to a nutrient medium for production, since aflastatin A is mainly found in the cultured mycelia, it is preferred to collect the mycelia by filtration or centrifugal separation of the culture medium, and then extract the aflastatin A from the strains by solvent extraction.

In the present invention, as the method for producing the salt of aflastatin A, various methods may be employed. For example, the following methods may be employed. Namely, at first, the aflastatin A as obtained above is contacted with or dissolved in a solution of a compound or an element which exhibits basicity in usual solvents, for example, organic ones such as dimethylamine, diethylamine or ammonia, or inorganic ones such as sodium, calcium or magnesium. Then, the reaction product is purified by a usual method, for example, recrystallization, precipitation or chromatography, to obtain a salt of the aflastatin A.

When the antibiotic aflastatin A and its salt of the present invention is used as a horticultural agent or a horticultural pesticide for the purpose of inhibiting aflatoxin, it can be formulated into the desired formulation such as granules, dusting powder, emulsion, wettable powder, tablets, lubricant, spraying agent or fuming agent for use, by using suitable solid carrier, liquid carrier, emulsifier or the like, as usual agricultural formulations. Among the carriers, as the solid carrier, clay, kaolin, bentonite, acid clay, diatomaceous earth, calcium carbonate, nitrocellulose, starch, carboxymethylcellulose and the like are preferably used. As the liquid carrier, water, methanol, ethanol, ethylene glycol, glycerol, dimethylsulfoxide and the like are preferably used.

Further, during the formulation, as the case requires, generally used adjuvants, for example, sulfates of higher alcohols, polyoxyethylenealkyl allyl ether, alkylally polyethylene glycol ester, alkylallyl sorbitan monolaurate, alkylally sulfonate, quaternary ammonium salt, polyalkylene oxide, and deoxycholic acid salt and its ester, may be incorporated.

When the antibiotic aflastatin A and its salt of the present invention is used as a horticultural agent or a horticultural pesticide, the proportion of the effective ingredient is controlled taking into consideration the types of the infection bacteria or pathogenic bacteria and extent of propagation thereof. However, in general, it is preferred to control the concentration to the level of from 10 to 5,000 ppm, preferably from 50 to 500 ppm for use.

Further, when the antibiotic aflastatin A and its salt of the present invention is used as an infection disease therapeutic pharmaceutical of human and animals (antimicrobial agent or antifungus agent) or an antitumor agent, it may be formulated into formulations such as tablets, granules, capsules or drops, by mixing it with appropriate pharmaceutically acceptable carrier, excipient or diluent by usual methods, and can be applied for the oral administration. Otherwise, it may be formulated into, for example, injections by usual methods, and incorporated into a sterilized carrier produced by usual methods, for the use of parenteral administration. Further, it may be used as an ointment by usual methods. When used as an injection, the dose a day is preferably from 0.3 to 3.0 mg/kg, preferably from 0.3 to 1.0 mg/kg.

The antibiotic aflastatin A and its salt of the present invention can be expected to be used as an intermediate for synthesis of novel pharmaceuticals, agricultural agents or animal agents.

The present invention will be described in further detail with reference to examples. However, it should be mentioned that the present invention is not limited to these. In the examples, "%" in medium represents weight/volume % unless otherwise specified.

EXAMPLE 1

(Production of aflastatin A)

125 ml of a liquid seed medium containing 3% of glucose, 1.5% of soy bean meal, 0.08% of $K_2HPO_4$, 0.02% of $MgSO_4 \cdot 7H_2O$, 0.4% of $CaCO_3$, was adjusted to pH 7.20, and then poured into each of 500 ml-Erlenmeyer flasks, followed by sterilization at 121° C. for 15 minutes.

Then, on the sterilized medium, one platinum loop of Spreptomyces sp. MRI 142 strain (FERM BP-5841) on a matured slant culture was inoculated. The flask was shaken by a rotary shaker at 27° C. for 42 hours with a 5 cm throw at 160 rpm.

Separately, 4 liters of a liquid production medium material 1 (hereinafter referred to as medium material 1) containing 1.875% of soy bean meal, 0.1% of $K_2HPO_4$, 0.025% of $MgSO_4 \cdot 7H_2O$, 0.5% of $CaCO_3$, was adjusted to pH 7.20, and then poured into a 10 liters-jar fermentor, followed by sterilization at 121° C. for 20 minutes. Further, 1 liter of a liquid production medium material 2 (hereinafter referred to as medium material 2) was sterilized at 121° C. for 20 minutes separately from the medium material 1.

The sterilized medium materials 1 and 2 were cooled to not more than 60° C., and then whole amount of the medium material 2 was added under sterilized condition into a 10 liters-jar fermentor having the medium material 1 placed.

Then, 250 ml of the above liquid seed medium was inoculated on 5 liters of the above liquid production medium, followed by cultivation at 27° C. for 144 hours with the supply of air at a rate of 5 liters/min. with stirring of 400 rpm. During the cultivation, an anti-foaming agent "Ainol" (tradename, manufactured by Aible K.K.) was automatically dropwise added by an automatic anti-foaming agent dropping device.

4.3 liters of the resulting culture broth was filtered by a filter paper "Toyo Roshi No. 2" (manufactured by Toyo Roshi K.K.), and the mycelial cake on the filter paper was collected by washing with 1 liter of distilled water. Then, the obtained mycelial cake was dipped in 1.2 liters of methanol and stirred at 65° C. for 1 hour for solvent extraction, followed by filtration by a glass filter to separate the extract from the mycelial cake. Then, the recovered mycelial cake was subjected to extraction operation further two times with methanol under the same conditions as above.

The whole amount of the resulting extracts (3.3 liters) were concentrated at 60° C. under reduced pressure to obtain 29.3 g of brown tar-like substance. The tar-like substance was dissolved in 600 ml butanol saturated with water and washed twice with 300 ml of 0.5 w/v % sodium bicarbonate with a separately funnel, followed by washing with 300 ml of distilled water to recover a butanol layer (an upper layer). Then, the recovered butanol layer was concentrated at 60° C. under reduced pressure to obtain 21.9 g of a brown oily substance.

To the oily substance, 500 ml of tetrahydrofuran was poured to obtain a precipitate. This precipitate was left to stand in the dark at room temperature overnight for maturity of the precipitate, and then subjected to filtration by a glass filter. 100 ml of tetrahydrofuran was poured on the glass filter for washing and recovering the precipitate substance on the filter. Then, the recovered precipitate was dried at room temperature in air in the dark to obtain 800 mg of slightly yellow powder.

This powder was suspended in a mixed solution of chloroform-methanol (2:1) and vigorously stirred for dissolution of impurities, and then the impurities were filtrated off by a glass filter, followed by washing with 50 ml of methanol. The washing operation with the mixed solution of chloroform-methanol was repeated twice, and the recovered insoluble was dried in air in the dark to obtain 632 mg of aflastatin A having a purity of 98.4%.

20 mg of the resulting aflastatin A was dissolved in 30 ml of a mixed solution of a 0.5 v/v % diethylamine aqueous solution and methanol (4:6), and filtrated by a filter "Milex FG" (tradename, manufactured by Nihon Millipore Ltd.). Then, 2 ml thereof was subjected to high performance liquid chromatography using a reverse phase column "CAPCEL L PACK 18 AG120" (tradename, manufactured by Shiseido) with 15 mm in diameter and 250 mm in length. Elution was carried out at room temperature with a mixed solution of a 0.5 v/v % diethylamine aqueous solution and methanol (35:65) at a flow rate of 5.0 ml/min., whereupon a single peak of aflastatin A was observed at around 8.5 minutes. The operation of recovering the single peak was repeated 15 times, and the recovered fractions were concentrated under reduced pressure, followed by lyophilization to obtain 14.2 mg of a diethylamine salt of aflastatin A.

In the above operation, since the solubility of the aflastatin A in the developing solvent was limitative, it was impossible to treat whole amount of 632 mg of the purified aflastatin A obtained from 4.3 liters of the culture with the high performance liquid chromatography. Theoretically, however, by the repetition of the above operation, about 449 mg of a diethylamine salt of aflastatin A is to be obtained from 632 mg of purified aflastatin A, namely, 4.3 liters of the culture.

EXAMPLE 2

(Aflatoxin production inhibitory activity of aflastatin A)

Spores of Aspergillus parasiticus NRRL 2999 strains as aflatoxigenic fungi, which were cultured on a slant medium of potato dextrose agar (manufactured by Nihon Suisan K.K.) at 27° C. for 21 days, were scrapped off and suspended in an aqueous solution of a 0.01% sufactant "Tween 80"

(tradename, manufactured by ICI Co.) which was sterilized at 121° C. for 15 minutes to prepare a spore suspension.

5.0 mg of the aflastatin A obtained in Example 1 was dissolved in 10 ml of dimethylsulfoxide for dilution, and then filtrated by a sterilized filter "Dimex" (tradename, manufactured by Nihon Millipore Ltd.), followed by sterilization to prepare a test solution.

10 μl of the test solution was sterilized at 121° C. for 15 minutes, added to 10 ml of potato dextrose agar (manufactured by Nihon Suisan K.K.), stirred and then poured into sterilized Petri dish having an internal diameter of 9 cm, to prepare dilution series plates of agar medium of the test solution. At this time, the final concentration of the aflastatin A was 0.5 μg/ml, 0.125 μg/ml or 0.031 μg/ml. As a control, 10 μl of dimethylsulfoxide was added to 10 ml of potato dextrose agar in the same manner as the above. As described above, three pieces of each of test plates and control plates having respective concentrations were prepared.

On one point at the center of each plate, 10 μl of the spores suspension obtained above was inoculated. The number of the inoculated strains was $2.5 \times 10^4$ per plate.

These plates were incubated at 27° C. for 7 days. At the 7th day, the growth conditions of the aflatoxigenic fungi were observed by measuring the diameter of colonies. Then, whole amount of the agar medium including strains were scrapped off the Petri dishes for the measurement test of aflatoxin.

Quantitative determination of the aflatoxin was carried out in accordance with the method described in J. Assoc. Off. Anal. Chem., 68, 458–461 (1985). Namely, to the samples scrapped off the Petri dishes, 80 ml of chloroform was added and vigorously stirred by a Warning blender for extraction of aflatoxin, and then filtrated by a filter paper "Toyo Roshi No. 5A" (tradename, Toyo Roshi K.K.) for recovery of the extract, followed by addition of anhydrous sodium sulfate for dehydration. 20 ml of this extract was collected by using a pipette, and subjected to a florisil column "SEP-PAK FLORISIL CARTRIDGES" (tradename, Nihon Millipore Ltd.,). Then, the column was washed with 30 ml of a mixed solution of chloroform and methanol (9:1), and eluted with 50 ml of a mixed solution of acetone and water (99:1) to recover the aflatoxin. Then, the elute of the mixed solution of acetone and water (99:1) was dried to dryness under reduced pressure to prepare a test sample for high performance liquid chromatography.

The above operations were carried out under a fluorescent lamp which generates no ultraviolet rays, and brown glass appliances were used.

Then, the above test sample was dissolved in 5 ml of a mixed solution of tetrahydrofuran, water and acetic acid, and 25 μl thereof was subjected to a column for high performance liquid chromatography "COSMOSIL 5-Phenyl" (tradename, Nakarai Tesk Co.) with 4.6 mm in diameter and 150 mm in length, followed by high performance liquid chromatography wherein elution was carried out at a flow rate of 0.8 ml/min. by using a mixed solution of tetrahydrofuran and water (20:80).

Quantitative determination of aflatoxin was carried out by comparing the area of isolated peak of 365 nm ultraviolet absorption with that of a standard product.

Aflatoxin production inhibitory activities of the aflastatin A are indicated in Table 3. In Table 3, the colony diameter and the aflatoxin concentration were represented by an average of triplicated experiments±standard deviation. Further, the aflatoxin concentration was calculated as the total of four homologues of aflatoxin, B1, G1, B2 and G2 (hereinafter the same applies).

TABLE 3

| Aflastatin A (μg/ml) | Colony diameter (cm) | Concentration of aflatoxin (total of B1, G1, B2 and G2 μg/ml) |
|---|---|---|
| Control (0) | 8.1 ± 0.1 | 13.75 ± 0.81 |
| 0.031 | 7.8 ± 0.2 | 7.10 ± 2.15 |
| 0.125 | 6.5 ± 0.2 | 0.82 ± 9.60 |
| 0.500 | 5.5 ± 0.3 | Not detected |

From the results given in Table 3, by the addition of aflastatin A or the increase of the concentration of aflastatin A, the production of aflatoxin can be remarkably reduced.

EXAMPLE 3

(Aflatoxin contamination inhibitory effect of aflastatin A)

Into horticultural planters with 55 cm in length, 30 cm in width and 32 cm in depth, a soil mixture of light clay, humus and loamy sand, was placed, and then dolomite was added in an amount of 25 g per planter.

At the center of the planter, one peanut seed of US-Florunner species was seeded, and cultivated outdoors while appropriately sprinkling water. After about 1.5 months from the seeding, the first bloom was confirmed, and after about 2 months from the seeding, the first penetration of gynophore into the soil was confirmed. Cultivation was further continued, its grains were matured and the cultivation lasted by 6 months from the seeding.

On the other hand, a solution having aflastatin A dissolved in dimethylsulfoxide at a proportion of 10 mg of the aflastatin A per 1 ml of dimethylsulfoxide, and a solution at a proportion of 2 mg of the aflastatin A per 1 ml of dimethylsulfoxide, were prepared as test solutions.

For the preparation of spraying solutions, each of the above test solutions was incorporated at a proportion of 1 ml to 40 ml of an aqueous solution for dilution containing 10 v/v % of glycerol, 0.1 w/v % of sodium deoxycholate and 0.01 v/v % of a horticultural spreader "Dain" (tradename, manufactured by Takeda Yakuhin Kogyo K.K.). Further, as a control, a solution having dimethylsulfoxide incorporated at a proportion of 1 ml to 40 ml of the same aqueous solution for dilution as above, was prepared.

On the foliage of peanut plants cultivated above, the above spraying solution was uniformly sprayed by a spray in an amount of 40 ml per plant. The sprayed amount of the aflastatin A at this time was 10 mg, 2 mg or 0 mg per peanut plant.

These peanut plants were left to stand outdoors for three days, and digged up, and then their root areas were washed with water. Then, the water was strained out, the whole raw weight of the peanut plants was measured, and then grains of peanuts were harvested with shells and the whole number thereof and the whole raw weight were measured.

Then, the shell surfaces of the measured peanut grains were wiped with 70 v/v % ethanol for sterilization, the shells were shucked in a manner as sterile as possible, and the peanut grains were taken out of the shells. Seven pieces were taken at random from these grains, and cut between two cotyledons. The weight of the peanut grains thus obtained was measured and then placed into a sterilized Petri dish.

On the surface of peanut grains placed in the Petri dish, sprayed was 300 μl of a spore suspension of *Aspergillus*

*parasiticus* NRRL 2999 as an aflatoxigenic fungus prepared in the same manner as in Example 2. Then, the dish was joggled for uniform inoculation of the aflatoxigenic fungus. The number of inoculated strains at this time was $3.0 \times 10^6$/dish.

After the inoculation, cultivation was continued at 27° C. for 7 days, and the growth conditions of the strains at the 7th day were observed by naked eyes. Further, the quantitative determination of aflatoxin was carried out in the same manner as in Example 2. The results are shown in Table 4. The growth conditions of the strains are evaluated by the following standards:

−: no growth, +: growth delayed, ++: fine growth

TABLE 4

| Aflatoxin A (mg/individual) | 0 (Control) | 2 | 10 |
|---|---|---|---|
| Weight of plants (g) | 485.1 | 413.5 | 432.1 |
| Weight of grains with shells (g) | 213.7 | 167.4 | 192.8 |
| Number of grains with shells (number) | 76 | 60 | 66 |
| Weight of seven pieces of peanut grains (g) | 11.0 | 11.6 | 11.5 |
| Growth of strains | ++ | ++ | ++ |
| Content of aflatoxin (total of B1, G1, B2 and G2, μg/g) | 10.51 | 6.09 | 0.19 |

From the results given in Table 4, the growth of strains is excellent in every case. However, the aflatoxin content can be remarkably reduced by incorporating aflastatin A or increasing the incorporated amount thereof.

EXAMPLE 4

(Antitumor activity of aflastatin A)

BDFI mice having a weight of from 21.0 to 24.3 g were divided into four groups each being 6 mice. A physiological saline suspension of adenocarcinoma 755 cells collected from subcultured 11th day mouse and adjusted, was transplanted subcutaneously at a right ventral portion of each mouse at a rate of $5 \times 10^5$ cells/0.5 ml/mouse.

The day of transplantation was regarded as the day 0. From the next day, intraperitoneal administration was carried out once a day for four successive days to each group at a rate of aflastatin A administration of 0.3 mg/kg/day, 1 mg/kg/day, or 3 mg/kg/day. The aflastatin A was suspended in a 0.25% carboxymethyl cellulose solution (manufactured by Nakarai Tesk) and administered at a dose of 10 ml/kg. The rest of the four groups was used as a control.

By the day 14, general conditions were observed every day, and the mice were clubbed to death at the day 14. Solid tumors were collected and their wet weights were measured. From the measured tumor weights, inhibitory ratios against the control group were calculated and antitumor activities were determined. The results are shown in Table 5. The tumor weight is represented by an average of six mice±standard deviation.

TABLE 5

| Dose of aflastatin A (mg/kg/day) | Weight of tumor (mg) | Antitumor activity (%) |
|---|---|---|
| Control (0) | 1617.8 ± 179.07 | 100.0 |
| 0.3 | 680.2 ± 176.63 | 42.0 |
| 1 | 392.8 ± 87.07 | 24.3 |
| 3 | All mice died by the day 3 | — |

From the results given in Table 5, the propagation of the transplanted mouse adenocarcinoma 755 can remarkably be inhibited when the aflastatin A was administered at doses of 0.3 mg/kg/day and 1 mg/kg/day. Further, the dose of 1 mg/kg/day shows a higher inhibitory effect rather than the dose of 0.3 mg/kg/day. However, the dose of 3 mg/kg/day is confirmed to be overdose.

As described above, the antibiotic aflastatin A or its salt of the present invention, has excellent aflatoxin contamination inhibitory effects and is effective as an antimicrobial agent, an antifungus agent and an antitumor agent.

What is claimed is:

1. An antibiotic aflastatin A having the formula:

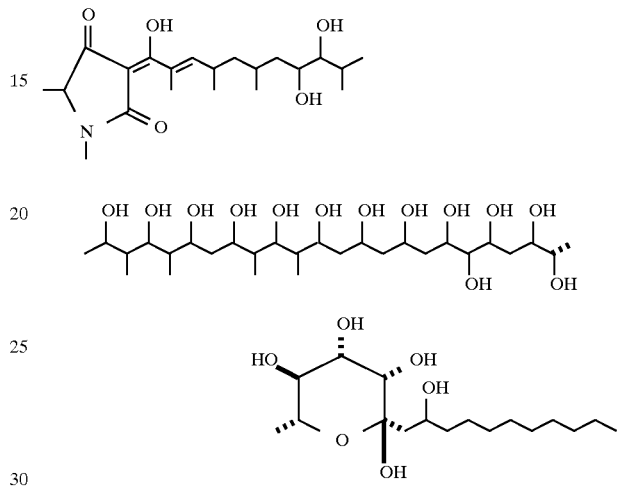

or its salt.

2. An aflatoxin contamination inhibitor comprising the antibiotic aflastatin A or its salt according to claim 1 and a carrier selected from the group consisting of a solid carrier, a liquid carrier and an emulsion dispersant carrier.

3. The aflatoxin contamination inhibitor according to claim 2, wherein the solid carrier is selected from the group consisting of clay, kaolin, bentonite, acid clay, diatomaceous earth, calcium carbonate, nitrocellulose, starch and carboxymethylcellulose, or wherein the liquid carrier is selected from the group consisting of water, methanol, ethanol, ethylene glycol, glycerol and dimethylsulfoxide.

4. The aflatoxin contamination inhibitor according to claim 2, wherein the antibiotic aflastatin A or its salt according to claim 1 is in an amount of from 10 to 5,000 ppm.

5. An antimicrobial agent comprising the antibiotic aflastatin A or its salt according to claim 1 and a pharmaceutically acceptable carrier, an excipient or a diluent.

6. An antifungus agent comprising the antibiotic aflastatin A or its salt according to claim 1 and a pharmaceutically acceptable carrier, an excipient or a diluent.

7. An antitumor agent comprising the antibiotic aflastatin A or its salt according to claim 1 and a pharmaceutically acceptable carrier, an excipient or a diluent.

8. A method for inhibiting aflatoxin contamination, which comprises spraying a composition comprising from 10 to 5,000 ppm of the antibiotic aflastatin A or its salt according to claim 1 on plants.

9. A method of inhibiting tumors, which comprises administering an effective amount of the antibiotic aflastatin A or its salt according to claim 1 to an animal in need thereof.

10. The method according to claim 9, wherein the antibiotic aflastatin A or its salt according to claim 1 is administered by injection in an amount of from 0.3 to 3.0 mg per kg of weight of the animal.

11. A process for preparing the antibiotic aflastatin A or its salt according to claim 1, comprising culturing a bacterial strain having all of the identifying characteristics of Streptomyces sp. MRI 142, FERM BP-5841, wherein said strain produces antibiotic aflastatin A, and isolating antibiotic aflastatin A or its salt from the culture medium.

12. The process according to claim 11, wherein the strain is Streptomyces sp. MRI 142, FERM BP-584.

13. The process according to claim 11, wherein the strain is a mutant of Streptomyces sp. MRI 142, FERM BP-5841.

* * * * *